United States Patent
Ahmed et al.

(10) Patent No.: US 11,969,442 B1
(45) Date of Patent: Apr. 30, 2024

(54) COVID-19 BINDING AEROSOLS

(71) Applicant: KING FAISAL UNIVERSITY, Al-Ahsa (SA)

(72) Inventors: Hany Mohamed Abd El-Lateef Ahmed, Al-Ahsa (SA); Saadeldin Elsayed Ibrahim Shabaan, Al-Ahsa (SA); Jihad Wadai Saleh Alessa, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/219,526

(22) Filed: Jul. 7, 2023

Related U.S. Application Data

(62) Division of application No. 18/120,305, filed on Mar. 10, 2023, now Pat. No. 11,813,287.

(51) Int. Cl.

| | |
|---|---|
| *A61K 33/26* | (2006.01) |
| *A61K 9/12* | (2006.01) |
| *A61K 31/245* | (2006.01) |
| *A61K 36/14* | (2006.01) |
| *A61K 36/54* | (2006.01) |
| *A61K 47/46* | (2006.01) |

(52) U.S. Cl.
CPC ............ *A61K 33/26* (2013.01); *A61K 9/12* (2013.01); *A61K 31/245* (2013.01); *A61K 36/14* (2013.01); *A61K 36/54* (2013.01); *A61K 47/46* (2013.01)

(58) Field of Classification Search
CPC ...... A61K 33/26; A61K 31/245; A61K 36/14; A61K 9/12; A61K 36/54; A61K 47/46
See application file for complete search history.

(56) References Cited

U.S. PATENT DOCUMENTS

| | | |
|---|---|---|
| 2021/0178106 A1 | 6/2021 | Glenn |
| 2021/0290718 A1 | 9/2021 | Hazan |
| 2021/0330635 A1 | 10/2021 | Borody |
| 2022/0000993 A1 | 1/2022 | Khanykov |

FOREIGN PATENT DOCUMENTS

| | | |
|---|---|---|
| AU | 2021106785 A4 | 11/2021 |
| KR | 20040010390 A | 1/2004 |
| WO | 2021207149 A1 | 10/2021 |
| WO | 2021231898 A1 | 11/2021 |
| WO | 2021242123 A1 | 12/2021 |

OTHER PUBLICATIONS

Sharfstein, John Hopkins Bloomberg School of health (Jun. 30, 202).*
Priyadarsini et al., "Nanoparticle Conjugates of Selenium Compounds: Preparation, Characterisation and Electron Transfer," Presented at the 1st International Electronic Conference on Catalysis Sciences, Nov. 10-30, 2020.
He et al., "Using nano-selenium to combat Coronavirus Disease 2019 (COVID-19)?," Nano Today. Feb. 2021; 36: 101037.
Abate et al., "Metal-Based Compounds in Antiviral Therapy," Biomolecules 2022, 12, 933.

* cited by examiner

*Primary Examiner* — Shirley V Gembeh
(74) *Attorney, Agent, or Firm* — Nath, Goldberg & Meyer; Richard C. Litman

(57) ABSTRACT

Covid-19 binding aerosols are provided. The Covid-19 binding aerosols include $Fe_3O_4$ microparticles, at least one organoselenium compound, at least one essential oil, and incense. The Covid-19 binding aerosols may be formulated for use in any product that is capable of emitting aerosols, including but not limited to as air fresheners, as incense, or the like. The $Fe_3O_4$ microparticles may have an average size of 5,000 nm-10,000 nm (between 5-10 μm). The Covid-19 binding aerosols are formulated as aerosol compositions having an average size of greater than 60 μm-100 μm to ensure effective binding to virions.

8 Claims, No Drawings

COVID-19 BINDING AEROSOLS

CROSS-REFERENCE TO RELATED APPLICATION

This application is a divisional of U.S. patent application Ser. No. 18/120,305, filed on Mar. 10, 2023, the contents of which are hereby incorporated by reference in their entirety.

BACKGROUND

1. Field

The disclosure of the present patent application relates to SARS-CoV2 ("Covid-19") binding aerosols.

2. Description of the Related Art

In general, Covid-19 is understood to transmit primarily through exposure to infectious respirator droplets and aerosol particles. While vaccination has proved effective in reducing the risk of life-threatening outcomes form Covid-19 infection, it has largely proved ineffective at preventing infection and preventing the spread of Covid-19 throughout the global population.

Common mitigation techniques for preventing the spread of Covid-19 have included the use of physical distancing, masking, and improved ventilation of enclosed spaces. While each of these techniques reduces the risk of exposure to Covid-19, none of them have proven 100% effective.

Thus, Covid-19 binding aerosols solving the aforementioned problems is desired.

SUMMARY

The Covid-19 binding aerosols include $Fe_3O_4$ microparticles, at least one organoselenium compound, at least one essential oil, and incense. The Covid-19 binding aerosols may be formulated for use in any product that is capable of emitting aerosols, including but not limited to air fresheners, as incense, or the like.

These and other features of the present subject matter will become readily apparent upon further review of the following specification.

DETAILED DESCRIPTION OF THE PREFERRED EMBODIMENTS

The Covid-19 binding aerosols include $Fe_3O_4$ microparticles, at least one organoselenium compound, at least one essential oil, and incense. The Covid-19 binding aerosols may be formulated for use in any product that is capable of emitting aerosols, including but not limited to air fresheners, as incense, or the like. The $Fe_3O_4$ microparticles may have an average size ranging from about 5,000 to about 10,000 nm (about 5-10 μm). The Covid-19 binding aerosols are formulated as aerosol compositions having an average size greater than respiratory droplets to ensure effective binding to virions and to, thereby, inactivate the virions. Respiratory droplets typically range in size from about 60 μm to about 100 μm.

The $Fe_3O_4$ microparticles may be synthesized by reduction of a sol of $Fe_3O_4$ with one or more of the organoselenium compounds, followed by spray drying. Specifically, the spray drying may include spraying the $Fe_3O_4$ organoselenium compounds into a fine droplet by an air assisted jet under a controlled pressure of 0.1 MPa. The resulting droplets may undergo evaporation, decomposition, and eventually be frozen into nano structures under a controlled temperature of 350° C. under an inert atmosphere for about 2.5 hours.

The resulting $Fe_3O_4$/organoselenium nanoparticles may be mixed with at least one essential oil and incense to form the Covid-19 binding aerosols. The essential oil used may be an essential oil from any plant that has demonstrated an anti-viral activity. For example, the essential oil may be from *Artemisia vulgaris* L., *Artemesia kermanensis* Podlech, *Cinnamomum zeylanicum* Blume, *Laurus nobilis*, *Juniperus oxycedrus*, *Aloysia gratissima*, *Citrus bergamia* Risso et Poiteau, or the like. In an embodiment, the Covid-19 binding aerosols may include an essential oil of *Laurus nobilis*, *Juniperus oxycedrus*, or a combination thereof. In an embodiment, the Covid-19 binding aerosols may include incense made from musk or sandalwood.

In an embodiment, the Covid-19 binding aerosols may comprise about 35% w/w $Fe_3O_4$, about 5% w/w organoselenium compounds, about 35% w/w/ essential oils; and about 25% w/w incense. The organoselenium compounds may be mixed with the $Fe_3O_4$ to produce $Fe_3O_4$ nanoparticles on an organoselenium backbone, and these particles may then be mixed with the essential oil and incense to form a colloidal solution. The colloidal solution may then be sprayed into a fine droplet by an air assisted jet (under a controlled pressure of 0/1 MPa). The resulting Covid-19 binding aerosol composition may then be formulated for use with an air freshener, and incense burner, or the like.

The organoselenium compounds used may be any organoselenium compound according to either Formula 1 or Formula 2, provided below:

FORMULA 1 wherein Y is H, carboxyl, methoxycarbonyl, or ethoxycarbonyl, and Z is H, $NO_2$, F, CN, or $OCH_3$; or

FORMULA 2 wherein Y is H, carboxyl, methoxycarbonyl, or ethoxycarbonyl, and Z is $NO_2$, F, CN, or $OCH_3$.

The organoselenium compounds may be synthesized according to Reaction 1 or Reaction 2, provided below

REACTION 1

[Reaction 1 scheme showing diselenide with two aminophenyl groups bearing Y substituents reacting with S=C=N-phenyl-Z in CH₂Cl₂ to form a bis-thiourea diselenide product]

wherein Y may be H, carboxyl, methoxycarbonyl, or ethoxycarbonyl, and Z may be H, NO₂, F, CN, or OCH₃; or

REACTION 2

[Reaction 2 scheme showing amine reacting with salicylaldehyde derivative in CH₃COOH to form bis-Schiff base diselenide product]

wherein Y may be H, carboxyl, methoxycarbonyl, or ethoxycarbonyl, and Z may be NO₂, F, CN, or OCH₃.

In an embodiment, the Covid-19 binding aerosols may be dispensed by aerosol spray dispensers. The aerosol spray dispensers may use eco-friendly compressed gases, e.g., oxygen and nitrogen, to dispense the Covid-19 binding aerosols while avoiding any possible environmental pollution.

The present teachings may be better understood in view of the following examples.

Example 1

Synthesis of dimethyl 5,5'-diselanediylbis(2-(3-(4-nitrophenyl)thioureido)benzoate)

Methyl 2-amino-5-selenocyanatobenzoateb was obtained from the selenocyanates of methyl 12-aminobenzoate via reaction with SeO₂ and malononitrile in DMSO at room temperature, as provided in the reaction scheme (Reaction 3), provided below. Hydrolysis of the selenocyanate under basic conditions produced dimenthyl 5,5'-diselanediylbis(2-aminobenzoate). The reactions of equimolar amounts of isothicyanato-4-nitrobenzene and diselenide 3 in dichloromethane and at room temperature resulted in the synthesis of dimethyl 5,5'-diselanediylbis(2-(3-(4-nitrophenyl)thioureido)benzoate) (Reaction 3).

REACTION 3

[Reaction 3 scheme showing methyl 2-amino-5-selenocyanatobenzoate converted via SeO₂, (CH₂)₂(CN)₂, DMSO, then NaOH, EtOH to diselenide, then reacted with S=C=N-C₆H₄-NO₂ in CH₂Cl₂ to give final bis-thiourea diselenide product]

It is to be understood that the Covid-19 binding aerosols are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of treating Covid-19 by binding Covid-19 aerosol particles, comprising dispensing an aerosol composition into the air as droplets, whereby the composition droplets bind to Covid-19 aerosol droplets, wherein the aerosol composition comprises Fe₃O₄ microparticles, at least one organoselenium compound, at least one essential oil, and incense; wherein the at least one organoselenium compound comprises either a compound according to the formula:

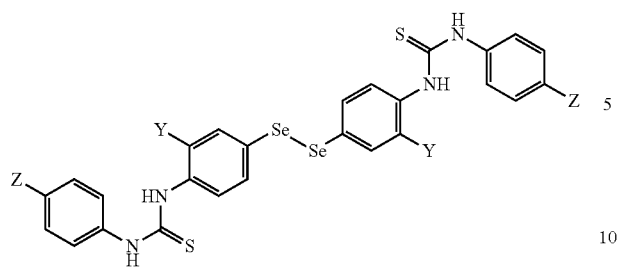
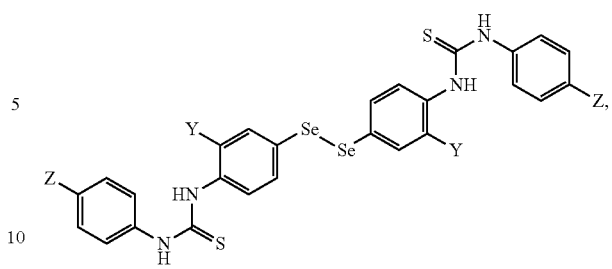

wherein
Y is selected from the group consisting of H, carboxyl, methoxycarbonyl, ethoxycarbonyl, and
Z is selected from the group consisting of H, NO$_2$, F, CN, and OCH$_3$; or
a compound according to the formula:

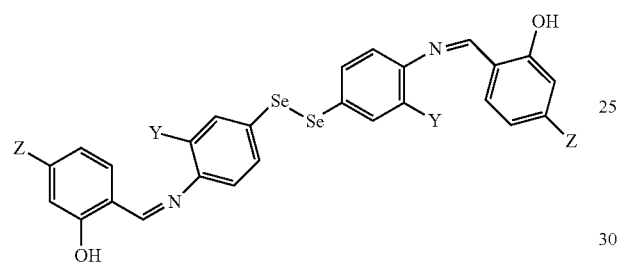

wherein
Y is selected from the group consisting of H, carboxyl, methoxycarbonyl, and ethoxycarbonyl, and
Z is selected from the group consisting of NO$_2$, F, CN, and OCH$_3$; and
wherein the at least one essential oil comprises an essential oil extract from a plant selected from the group consisting of *Artemisia vulgaris* L., *Artemesia kermanensis* Podlech, *Cinnamomum zeylanicum* Blume, *Laurus nobilis*, *Aloysia gratissima*, *Juniperus oxycedrus*, and *Citrus bergamia* Risso et Poiteau.

2. The method of claim 1, wherein the Fe$_3$O$_4$ microparticles have an average particle size ranging from about 5 μm to about 10 μm.

3. The Method of claim 1, wherein the at least one organoselenium compound comprises a compound according to the formula:

wherein
Y is selected from the group consisting of H, carboxyl, methoxycarbonyl, ethoxycarbonyl, and
Z is selected from the group consisting of H, NO$_2$, F, CN, and OCH$_3$.

4. The method of claim 1, wherein the at least one organoselenium compound comprises a compound according to the formula:

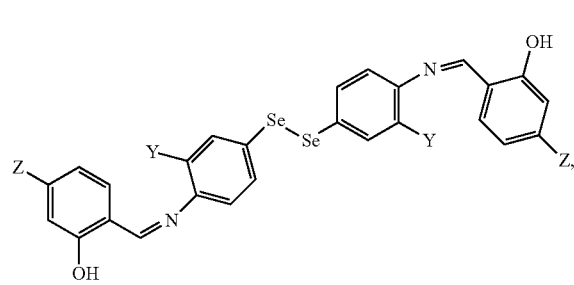

wherein
Y is selected from the group consisting of H, carboxyl, methoxycarbonyl, and ethoxycarbonyl, and
Z is selected from the group consisting of NO$_2$, F, CN, and OCH$_3$.

5. The method of claim 1, wherein the at least one essential oil comprises an essential oil of *Laurus nobilis*.

6. The method of claim 1, wherein the at least one essential oil comprises an essential oil of *Juniperus oxycedrus*.

7. The method of claim 1, wherein the at least one incense comprises an incense selected from the group consisting of musk and sandalwood.

8. The method of claim 1, wherein the composition comprises about 35% w/w Fe$_3$O$_4$, about 5% w/w organoselenium compounds, about 35% w/w/ essential oils; and about 25% w/w incense.

* * * * *